United States Patent [19]
Tomic

[11] Patent Number: 5,145,368
[45] Date of Patent: Sep. 8, 1992

[54] SUCTION ROOT ELEVATOR AND SUCTION DENTAL CURETTE

[76] Inventor: Dobrivoje Tomic, Fasangartenstrasse 159, 8000 Munich 90, Fed. Rep. of Germany

[21] Appl. No.: 654,878

[22] Filed: Feb. 13, 1991

Related U.S. Application Data

[63] Continuation-in-part of Ser. No. 346,959, May 2, 1989, abandoned.

[51] Int. Cl.$^5$ ............... A61C 17/06; A61C 3/00
[52] U.S. Cl. ........................... 433/91; 433/95; 433/143; 433/141
[58] Field of Search ............ 433/91, 92, 93, 94, 433/95, 96, 141, 142, 143, 144

[56] References Cited

U.S. PATENT DOCUMENTS

| | | | |
|---|---|---|---|
| 1,345,606 | 7/1920 | Leonard | 433/92 |
| 2,531,730 | 11/1950 | Henderson | 433/91 |
| 2,715,899 | 8/1955 | MacLean | 433/142 |
| 4,568,332 | 2/1986 | Shippert | 433/95 |
| 4,822,278 | 4/1989 | Oliva et al. | 433/91 |
| 4,878,900 | 11/1989 | Sundt | 433/91 |

Primary Examiner—Cary E. O'Connor
Attorney, Agent, or Firm—Bucknam and Archer

[57] ABSTRACT

The invention relates to a suction root elevator and a suction dental curette each of which comprises a handle and a working part both of which are provided with a canal system which extends through both the handle and working part. The canal system terminates in an opening at the tip of the working part on one side while the opposite end of the canal is by means of a flexible connection attached to a suction unit. In addition to the integrated canal system an external pipe system may be attached running parallel to the longitudinal axis of the instrument terminating in an opening next to or distally of the working part's tip, while its opposite end is attached by means of a flexible connection to a rinsing device. The working end of the suction root elevator as well as the suction dental curette may be detachably secured to the handle thus permitting to be replaced by another similarly or differently shaped working part.

10 Claims, 2 Drawing Sheets

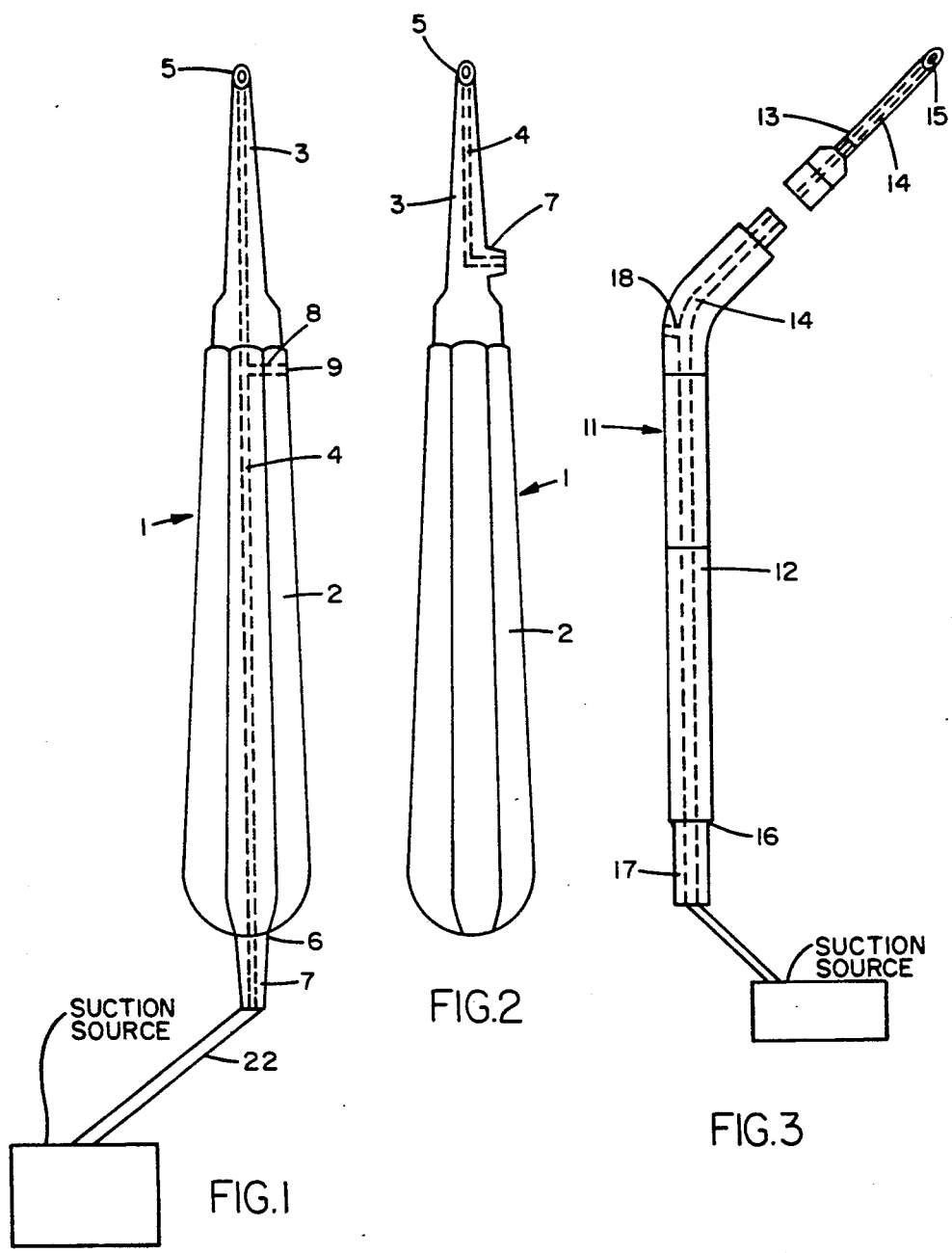
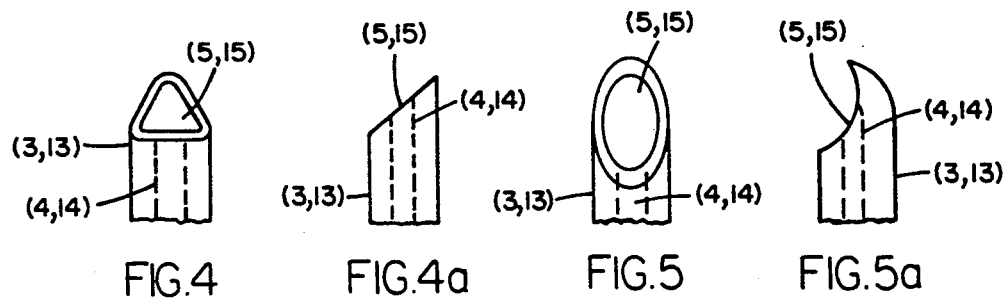
FIG.1  FIG.2  FIG.3
FIG.4  FIG.4a  FIG.5  FIG.5a

SUCTION ROOT ELEVATOR AND SUCTION DENTAL CURETTE

BACKGROUND OF THE INVENTION

This application is a continuation in part of Ser. No. 07/346,959, filed May 2, 1989, now abandoned.

The invention relates to a root elevator and dental curette, henceforth specified as suction root elevator and suction dental curette, both of which are to be used in dentistry, particularly in oral surgery and periodontology. A common characteristic to both instruments, signifying their uniqueness, is the presence of an integrated canal system which extends from the working tip of the instrument to its opposite end which by means of a flexible connection can be attached to a suction or rinsing unit/apparatus or both at the same time by means of an externally attached parallel pipe system which can be optionally affixed.

Traditional root levators as well as dental curettes are essential instruments in oral surgery and periodontology having a broad field of use in daily practice. However, due to their design which has remained virtually unchanged for decades the efficacy of these instruments is, to this date, largely dictated by the requirement for additional instruments as well as the presence of an assistant to the practitioner.

A root elevator in its various shapes is an instrument routinely used in oral surgery for the extraction of teeth, dental roots and fragments thereof, as well as the extraction of impacted teeth. However, the consequent presence of blood and continued salivation require that, in order to have a clear field of view, the practitioner hold two instruments simultaneously, that is, one for the dotting of bleeding and salivation, the other being the root elevator. In order to avoid the obvious awkwardness of such a working method the presence of an assistant is required who will dot the wound. Since the anatomical conditions of an extraction wound in the oral cavity hardly permit two separate instruments to be engaged simultaneously the practitioner must intermittently remove the root elevator in order that the assistant may gain access for dotting. Thus, precious time and work continuity is lost; furthermore the repeated search for a fragment previously located is on one hand tedious for the practitioner, on the other hand it presents a repeated traumatization of the wound exposing the patient to prolonged bleeding and fatiguing stress, with a higher risk of postoperative complications such as dry socket or infections of various etiology.

Periodontology, even though gaining in importance in modern dentistry, to this date relies on instrument conceived long ago. The traditional dental curette with its broad field of use, without exaggeration, presents one of the most important instruments in this branch of dentistry. This instrument finds use in the scaling of root surfaces of necrotic cementum, the curettaging of periodontal pockets and abscesses, the scraping off of granulomatous, sanguineous, necrotic and purulent masses, the scraping off of subgingival tartar and other operations similar in character. Beside this use in conservative periodontology it is used with equal frequency and for the same purpose in periodontic surgery. However, due to the fact that the traditional dental curette, as it is used up to this date, exists only as a singular instrument by itself, the practitioner has to use at least two instruments simultaneously. That is, aside from the principal instrument, the traditional curette, he would also have to hold one additional instrument for the aspiration of the sanguineous, necrotic and prulent masses which are set free as a result of the intervention and a third instrument for the rinsing of the wound. In view of the technical impossibility of such maneuvering the practitioner must rely on an assistant who will intermittently aspirate any blood, saliva and other organic debris and possibly rinse the wound to clear the obstructed field of view for the practitioner. The greatest drawback of such a periodontic operation, however, lies not merely in the need of several instruments but in the fact that the process of curettaging, aspiration and rinsing present at least two separate mechanical actions carried out by two persons. This consequent disruption in continuity results in the continuous remaining of organic debris in the wound itself which necessitates several sessions, an average of three to four, in order to obtain the desired result, namely the complete curing of a periodontal pocket and/or abcess. In the course of operation the delicate periodontal tissue is newly traumatized, requiring often long periods of recovery. Furthermore, one cannot ignore the factors time and financial burden for the patient which present an ever more significant argument in dental care planning.

In conclusion it can be said that both, the traditional root elevator as well as the traditional dental curette, as they are used to this date, present instruments which despite their proven validity show numerous disadvantages to the practitioner and more so to the patient.

SUMMARY OF THE INVENTION

The above described disadvantages are overcome by the instruments of the present invention, namely the suction root elevator and the suction dental curette, due to the presence of an integrated canal or pipe system common to both instruments which makes possible the simultaneous aspiration from the wound while the operation is being carried on. A second pipe system, externally affixed to the suction dental curette, as an option, further increases the versatility of the instrument because rinsing of the wound is made possible in addition to the previously mentioned simultaneous functions. Both, the suction root elevator and the suction dental curette which by means of a flexible connection, are attached to a suction unit or, in the case of the suction dental curette, to an additional rinsing unit, permit the practitioner to perform interventions as traditionally prescribed for either instrument, thus, making unecessary for additional instruments such as aspirators and/or rinsing cannules used up to this date to provide a clear field of view.

Thus, while using a suction root elevator to remove a fragmented tooth or its root, or fragment thereof as well as impacted teeth from an open wound, through the integrated canal system blood, saliva and organic debris are simultaneously aspirated from the wound, permitting the practitioner to have visual control over the intervention taking place in the wound. Furthermore, the practiotioner is no longer distracted by intermittent dotting and/or aspirating of the wound by an assistant, thus cutting the curation of the operation itself to a fraction of the time required to date. Above all, the incomparably greater comfort for the patient who will suffer considerably less trauma and whose bleeding time and amount will be contained to a minimum must be emphasized.

The suction dental curette greatly facilitates periodontic interventions since the mechanical removal of sanguineous, necrotic, granulomatous and purulent masses from periodontic pockets and abscesses as well as the scaling of root surfaces, the scraping off of subgingival tartar is accompanied by the simultaneous aspiration of the organic debris set free during the operation within the wound. Consequently, the possibility of organic debris remaining in a periodontic pocket, heretofore a frequent source of complications such as prolonged healing, continued inflammation and abscessing, is eliminated, which in turn reduces the number of therapy sessions per tooth and pocket to a single session intervention in most of the cases. The effect of the simultaneous aspiration can be further potentiated by affixing an optional external rinsing pipe by means of which the wound can be rinsed with water or with solutions frequently used in periodontics to create a disinfected area, such as hydrogen peroxide, or other similar solutins. In either event the patient experiences a minimum of trauma at the same time feeling almost instant relief, whereby recurrences, especially of periodontic abscesses are virtually eliminated due to the simultaneous removal and aspiration of possible infection agents as well as the rinsing of the wound. In addition, the healing process is accelerated due to the fact that all irritating factors (such as fragments of tartar, necrotic cement, etc.) have been removed from the periodontal pocket thus permitting an unimpaired process of tissue restoration.

Both instruments, namely the suction root elevator as well as the suction dental curette can be made of any material commonly used for similar purpose dental instruments and therefore can be fully sterilized in accordance with standard sterilization procedure. It is well known in the dental profession that in a curette the cutting edge is formed on the side of the tip.

BRIEF DESCRIPTION OF THE DRAWINGS

The following drawings shall further illustrate the present invention and claims.

FIG. 1 is a front elevation view of a suction root elevator according to the invention;

FIG. 2 shows a modified embodiment of the suction root elevator shown in FIG. 1;

FIG. 3 is an enlarged elevational view of a suction dental curette showing the instrument in profile according to the invention;

FIG. 4, 4a and FIG. 5, 5a present enlarged front and lateral views, respectively, of two different tips of the dental instruments shown in FIGS. 1, 2, and 3;

PREFERRED EMBODIMENTS OF THE INVENTION

Figures 6, 7:
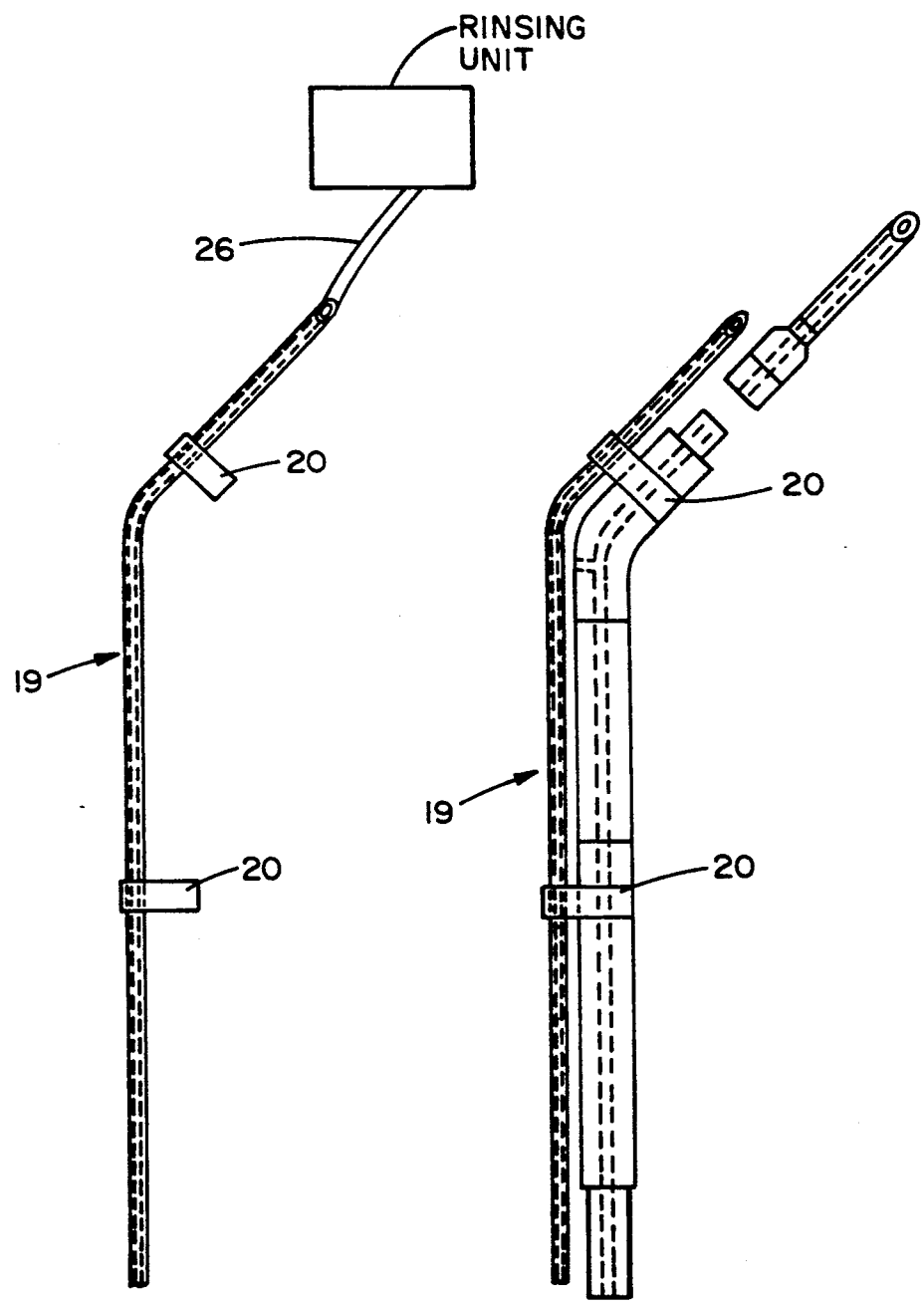
FIG. 6 presents an enlarged lateral elevational view of the rinsing pipe.
FIG. 7 shows an enlarged lateral elevational view of the suction dental curette as shown in FIG. 3 with the affixed rinsing pipe as presented in FIG. 6.

Preferred embodiments of this invention will now be described with reference to the drawings in detail. As is shown, the suction root elevator 1 externally presents an instrument not much different from traditional root elevators, comprising a handle 2 and a working part 3. The dotted lines running centrally through the length of the instrument depict the canal system 4, which opens at the tip 5 of the working part 3 on one side and at the distal end 6 of the handle on the opposite side. The distal end 6 of the handle is elongated in the shape of a cylinder 7 which permits a flexible connection, 22, to be attached to the handle of the instrument. The opposite end of the flexible connection is securely attached to a suction unit 24 which creates negative pressure, that is a vacuum, by which a suction effect is reached, whereby blood, saliva and organic debris are aspirated through the canal system of the root elevator 1. If desired, an additional duct 8, perpendicular to the principal duct 4, can be provided which opens on the side 9 of the handle 2, serving as a valve, permitting the practitioner to manipulate the presence or absence of vacuum on an on/off basis by digitally covering the opening 9 of the valve. Although not shown here it is understood by those skilled in the art that variations and modifications of the valve system can be equally installed.

The flexible connection leading from the root elevator to the suction unit can originate, instead of from the instrument's distal end, from the instrument's side whereby the exiting duct can be perpendicular to the principal duct as shown in FIG. 2 as well as in an obtuse angle not shown in the drawings.

To those skilled in the art it should be clear that the suction root elevator can be shaped as all commonly used traditional root elevators, such as root elevators according to Lecluse, Winter, Barry and numerous other authors. Furthermore, the instrument can be made of any material used in the prior art of the instrument as well as new materials which are proven in terms of their stability to mechanic forces such as pressure as well as to thermal forces such as those created during sterilization.

The suction dental curette 11 shown FIG. 3 of the drawings is an instrument comprising a handle 12 and a detachable working part 13. A canal system 14, extending from an opening 15 in the tip of the working part 13 to the distal end 16 of the handle 12, continues through a cylindrical elongation 17 of the handle 12 terminating in an opening at the cylinder's distal end. The detachable working part 13 of the instrument 11 can be replaced by another identically, similarly or differently shaped tip of the working part, an example of which is shown in FIGS. 4, 4a and 5, 5a, thus meeting the individual needs as dictated by the location of teeth and the morphology of the periodontal pockets and/or abscesses to be treated. Furthermore, the working part can be positioned in relation to the handle in a straight, obtuse or right angle in such way that interventions on pockets which are located in the inter-canine region are more conveniently carried out by a straight instrument, wheras for the trans-canine region an angled version of the instrument is more suitable.

Similar to the suction root elevator shown in FIG. 1 the suction dental curette 11 can also be provided with a valve duct 18 situated perpendicularly to the principal canal 14 and exiting at the side of the handle in the form of an orefice. The functional principle as well as the possible variations and modifications of the valve system mirror those of the suction root elevator.

The cylinder 17 extending from the distal end of the handle 16 is to fit into a flexible connection the opposite end of which is securely connected to a suction unit/apparatus which by way of negative pressure creates a vacuum. Said vacuum makes possible the simultaneous aspiration of blood, saliva and other organic debris which is produced by such periodontic operation. As an optional addition to the suction dental curette 11 and its integrated canal system 14 an external pipe system 19 can be attached to the instrument by clamps 20 or otherwise suitable detachable fittings. Said pipe system can be attached to the instrument whereby its tip ends approximately 15 mm distally of the tip of the suction dental curette so as not to interfere with the reaching ability of the curette's tip. Said pipe system shows two orefices, one the proximal end and another at the distal end whereby the latter is connected by flexible connection 26 to a rinsing unit 28. Said rinsing unit pumps from a container liquid solutions such as disinfectants or water which exits at the tip of the pipe system onto the immediate operating area irrigating the same in simultaneous action with the aspiration through the central canal system 14.

The material requirements for the suction dental curette as well as for the external pipe system equal those of the suction root elevator. That is any materials used in the prior art of this instrument as well as new materials giving the instruments sufficient mechanic rigidity so as not to be deformed or bent during the operation and further having the necessary thermal stability to endure full sterilization procedures. It is to be understood for both instruments, the suction root elevator and the suction dental curette, that the choice of material used also include such materials which permit for the instruments to be used as disposable, single use instruments. Both instruments, namely the suction root elevator and the suction dental curette, have been described mainly in reference to dental operations, particularly those of oral surgery and periodontology. It is to be understood, however, that said instruments can find equal use in the field of human medicine and veterinary medicine. To those skilled in the art it will be apparent that modifications and variations can substitute elements of the preferred embodiments described above without departing from the principles and true spirit of this invention.

I claim:

1. A root elevator for the extraction of teeth, roots or fragments thereof which consists of a handle (2), said handle having a proximal end and a distal end and a working part (3) located adjacent to said proximal end, said working part having a tip (5), a channel (4) extending through both said handle and said working part from said tip of the working part to the distal end of said handle, said root elevator having a first opening at said tip of the working part and a second opening at said distal end of said handle, a first flexible connecting means (22) connected to said second opening of said distal end, suction means connected to said flexible connecting means.

2. The root elevator according to claim 1 wherein said working part is detachable from the handle and replaceable.

3. The root elevator according to claim 1 wherein said working part and said handle are arranged at an obtuse angle to one another.

4. The root elevator according to claim 1 which is provided with valve means consisting of a duct (8) perpendicular to said channel and connected thereto.

5. The root elevator according to claim 1 which is provided with an external pipe system detachably affixed to said working part and extending parallel to said working part, and said pipe system has a rinsing unit attached thereto by second flexible connection means.

6. A root elevator for the extraction of teeth, roots and fragments thereof which consists of a handle (2) and a working part (3), said working part (3) having a tip (5), said tip having an opening, a channel (4) through said working part extending from said tip through a substantial part of said working part; a duct perpendicular to said channel, first flexible connection means connected to said duct and suction means connected to said connection means.

7. The root elevator according to claim 6 wherein said working part is detachable from the handle and replaceable.

8. The root elevator according to claim 6 wherein said working part and said handle are arranged at an obtuse angle to one another.

9. The root elevator according to claim 6 which is provided with an external pipe system detachably affixed to said working part and extending parallel to said working part, and said pipe system has a rinsing unit attached thereto by second flexible connection means.

10. A dental curette which consists of a handle (11) having a proximal end and a distal end, a working part (13) connected to said proximal end, a channel extending through both said handle and said working part, a duct (18) perpendicular to said handle, said working part having a tip (15), said curette having a first opening at said tip of the working part and a second opening at said distal end of said handle, a flexible connecting means connected to said second opening of said distal end, suction means connected to said flexible connecting means, said tip having a cutting edge formed on the side thereof.

* * * * *